United States Patent [19]

Krumeich

[11] Patent Number: 4,844,060
[45] Date of Patent: Jul. 4, 1989

[54] FIXATION RING FOR RADIAL KERATOTOMY

[76] Inventor: Jorg H. Krumeich, Propst-Hellmich-Promenade 28, 4630 Bochum 6, Fed. Rep. of Germany

[21] Appl. No.: 132,062

[22] Filed: Dec. 11, 1987

[30] Foreign Application Priority Data

Dec. 12, 1986 [DE] Fed. Rep. of Germany ....... 3642521

[51] Int. Cl.$^4$ ............................................. A61B 17/00
[52] U.S. Cl. ................................................ 128/303 R
[58] Field of Search .................... 128/303 R, 305, 325

[56] References Cited

U.S. PATENT DOCUMENTS

| | | | |
|---|---|---|---|
| 2,437,812 | 3/1948 | Freel | 128/303 R |
| 4,275,733 | 6/1981 | Mirinoff | 128/303 R |
| 4,406,285 | 9/1983 | Villasener et al. | 128/303 R |
| 4,440,168 | 4/1984 | Warren | 128/303 R |
| 4,542,742 | 9/1985 | Winkelman et al. | 128/303 R |
| 4,688,570 | 8/1987 | Kramer et al. | 128/305 |
| 4,739,761 | 4/1988 | Grandon | 128/303 R |

*Primary Examiner*—Max Hindenburg
*Attorney, Agent, or Firm*—Clifford Poff; Daniel Patch

[57] ABSTRACT

Instead of having the surgeon make cuts freehand in a radial keratotomy operation for correction of the refraction of the human cornea, there is provided a fixation ring which has an eccentrically located band or bridge, the side of which is toward the middle of the ring is formed as a vertical, planar positioning and guide surface, extending vertically with respect to the plane of the ring. This bridge can be mounted on the ring itself or fastened onto an inner ring that is freely rotatable with respect to an outer ring. Means for limiting the depth of the cut may also be provided. This makes it easier to obtain straight and regular cuts in the desired radial direction. Operations can be completed more quickly, and there is a better prognosis for obtaining the desired results in the operation.

6 Claims, 1 Drawing Sheet

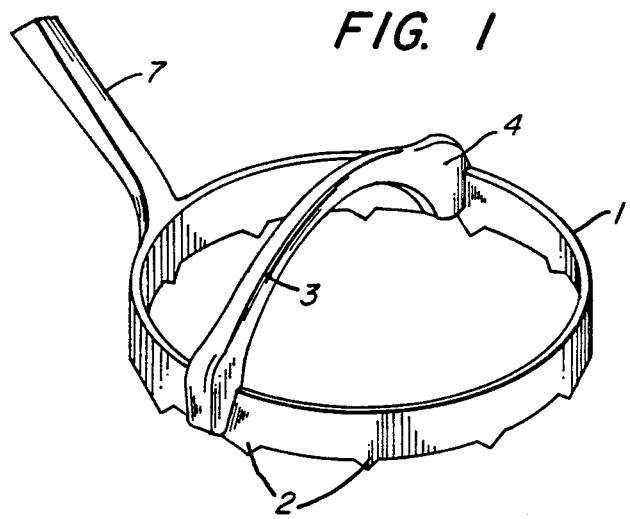
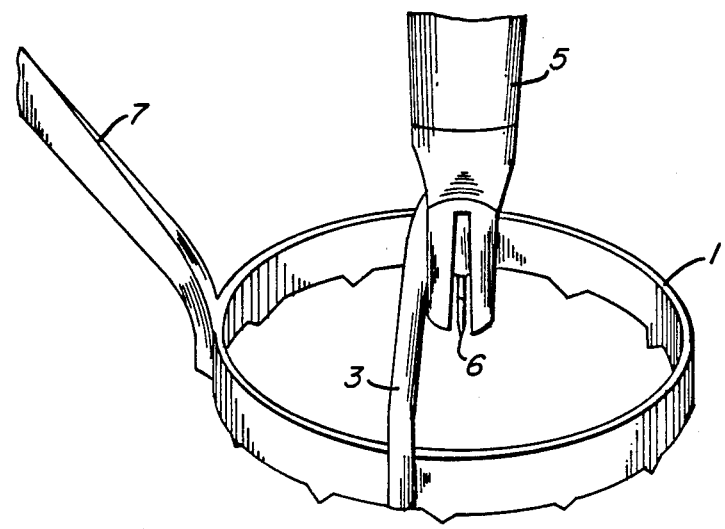
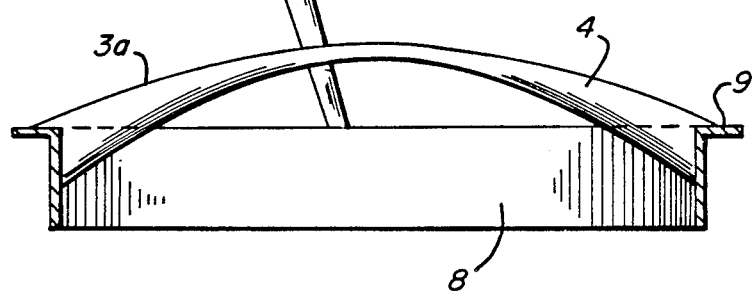

FIXATION RING FOR RADIAL KERATOTOMY

BACKGROUND OF THE INVENTION

1. Field of the Invention

This invention relates to a fixation ring for radial keratotomy, which affords teeth or is formed as a vacuum ring, for the temporary fixation or the immobilization of the human eye in situ.

2. Description of the Prior Art

The method of radial keratotomy is generally known in ophthalmology, and it serves for the modification of the refraction of the human cornea. In radial keratotomy, there are formed, with a cutting apparatus, such as a knife, cuts of a given depth in the cornea. Commonly, the cuts are between 0.05 and 0.65 millimeter deep. Such a method permits corrections of myopia up to about minus 8 diopters. By producing such cuts, a desired weakening of the cornea in its periphery is produced, so that it can be subjected to pressure from the inner pressure of the eye, and the cornea can thereby be flattened. With the flattening of the cornea, the refractive power of the eye is diminished, and the focal point is moved to the retina from the plane of the vitreous humor of the eye, in which it lies in the case of myopia. The desired effect of this method is among other things dependent upon the size of the uncut optical zone in the center of the cornea, as well as the depth and the length of the cuts.

Prior to the present invention, the cuts have been made free-hand, the surgeon moving a steel knife or a special cutting apparatus with a protruding diamond either from the periphery towards the center of the optical zone or the reverse. For the surgeon, it is particularly difficult to guide the knife always perpendicular to the tangent of the cornea's outer surface. However, if the knife contacts the cornea surface diagonally, there are developed other, uncalculable conditions, which can lead to an increased fluctuation in the results of the various operations.

BRIEF SUMMARY OF THE INVENTION

The invention solves the problem of improving or forming a fixation ring so that with a usual cutting apparatus, especially one for the formation of radial cuts in the cornea surface, it is possible in a simple way to obtain perpendicular guiding of the cutting apparatus with respect to the tangent of the cornea surface. This problem is solved, according to the invention, with a fixation ring for radial keratotomy which has on its ring, on the side opposite the eye, an eccentrically located band-like bridge, in which at least the side toward the middle point of the ring is formed as a vertically extending positioning and guide plane. The separation of the positioning and guide plane from the middle point of the ring is so proportioned that a knife or the like laid against it cuts with its knife point or edge the middle point of the ring.

The bridge can be fixed onto the fixation ring. In order to produce several radial cuts with such an apparatus, the fixation ring is rotated about its middle point for each desired radial cut.

It can also be advantageous to fasten the bridge with its ends on an inner ring, one which is freely rotatable with respect to the outer ring. Thereby, the inner ring can be formed, for example, as a flange ring and be held rotatably within the outer ring. With such an embodiment, for the positioning of the bridge in and individual desired cutting positions, only the inner ring needs to be turned. The outer ring, in contrast, holds its position on the cornea during the production of the desired cut. Advantageously, the inner ring contains a radial extending handgrip.

The advantage is that obtainable according to the invention consists in that the knife can, during the cutting movement along the positioning and guide surface of the bridge, be led adjacently as against a ruler or straightedge. Thereby, in contrast to the usual freehand cuts of the prior art, there are obtained cuts that are always perpendicular to the tangent of the cornea outer surface. As the bridge also can serve during the cutting movement for the positioning of the knife in respect to the depth of its cut, there may also then be obtained cuts of equal depths. All together, such a guiding of a knife makes possible functionally reproducible proportions and thereby an improved expectation of desired results. Moreover, such an operation can be conducted substantially more quickly, and possible repeat operations can be conducted in exactly the same cuts in the same positions. It may also be observed that the bridge can be positioned transversely with respect to radial cuts, in order to make possible the operations for the correction of astigmatism, for example, the Ruiz method or the T cuts. For cuts of this kind, the side of the bridge which is more remote or distal from the middle point can be used as the guide or positioning surface.

DESCRIPTION OF THE DRAWINGS

Embodiments of the invention are shown in the drawings, and will be further explained below.

FIG. 1 shows a perspective view of a fixation ring with a solidly affixed bridge according to the invention;

FIG. 2 shows a further perspective view of the fixation ring according to FIG. 1, with a juxtaposed cutting knife; and FIG. 3 shows a sectional view of a inner ring with a bridge fixed on it as a component for a fixation ring.

DESCRIPTION OF THE PREFERRED EMBODIMENTS

In the embodiment of the invention shown in the drawings, there is shown a metallic fixation ring for radial keratotomy, in which the ring (1) in its situs of use exhibits a number of equally spaced teeth (2) about its periphery. The diameter of such a ring (1) is ordinarily about 14 millimeters.

With the positioning of the ring (1) in the eye, the teeth (2) enter lightly into the tissue of the cornea, whereby with the help of the ring (1) there is effected the desired immobilization of the eye during the operation.

On the side of the ring (1) opposite to the eye, there is fastened an eccentrically located band-like solid bridge (3) with its ends on the ring (1). The affixation can be effected by a known means, such as a clip, welding, or the like.

The side of the bridge (3) which is toward the middle of the ring (1) is formed as a planar positioning and guide surface (4). As regard its direction, it stands vertical with respect to the plane of the ring. The radial separation of the positioning and guide surface (4) from the middle point of the ring (1) is so proportioned that a juxtaposed knife (5) cuts with its knife point or edge (6) the middle point of the ring 1 (see FIG. 2).

As is also illustrated in the drawing, there is fastened on the ring (1) on its periphery a grip part (7) with a radial portion, by means of which the ring (1) is placed and held.

Instead of fastening the bridge (3) onto the fixation ring, there can also be used an inner ring, which bears the bridge (3) and is freely rotatably situated on the fixation ring. Such an inner ring is shown in FIG. 3 and designated with the reference numeral (8). On its outer end, the inner ring (8) contains a radially outwardly extending lip (9), which form a ring flange with the inner ring (8) in its installation position on the outer rim of the ring, with which the eye is held during the operation. Also with this embodiment of the invention, the bridge (3a) is solidly affixed at its ends according to a suitable method to the inner ring (8).

As FIG. 3 shows, a radially extending hand grip (10) is provided on the inner ring (8). With the aid of this hand grip, the inner ring (8) can be rotated with respect to the anchored fixation ring and held for the execution of the desired cuts in a particular desired position of rotation.

While I have shown and described herein certain embodiments of my invention, I intend to cover as well as change or modification therein which may be made without departing from its spirit and scope.

I claim as my invention:

1. A fixation ring apparatus to guide a cutting device for radial keratotomy, said ring apparatus including a fixation ring including means at one side thereof for establishing a fixed positioning in respect to a human eye, and a bridge eccentrically arranged extending across said fixation ring at a side thereof opposite to said means for securing; said bridge having a vertical knife positioning and guide surface with respect to the plane of the fixation ring, said surface facing toward the middle point of said fixation ring.

2. A fixation ring apparatus according to claim 1 characterized in that the radial offset of the said positioning and guide surface from the middle point of the ring is so proportioned that a knife placed against said surface will with its knife edge cut the middle point of the said ring.

3. A fixation ring apparatus according to claim 2 characterized in that the bridge (3) is fastened on its ends to the fixation ring (1).

4. A fixation ring apparatus according to claim 2, wherein said fixation ring comprises an inner and outer rings and wherein said bridge is fastened at its ends on the inner ring which is situated freely rotatably on the outer ring.

5. A fixation ring apparatus according to claim 4, characterized in that the inner ring includes a flange ring rotatably in contact within the outer ring.

6. A fixation ring apparatus according to claim 5, further including a hand grip extending radially from an attachment site on said fixation ring.

* * * * *